March 25, 1969 J. H. ASPER Plant Pat. 2,874
CAMELLIA PLANT
Filed Sept. 1, 1967
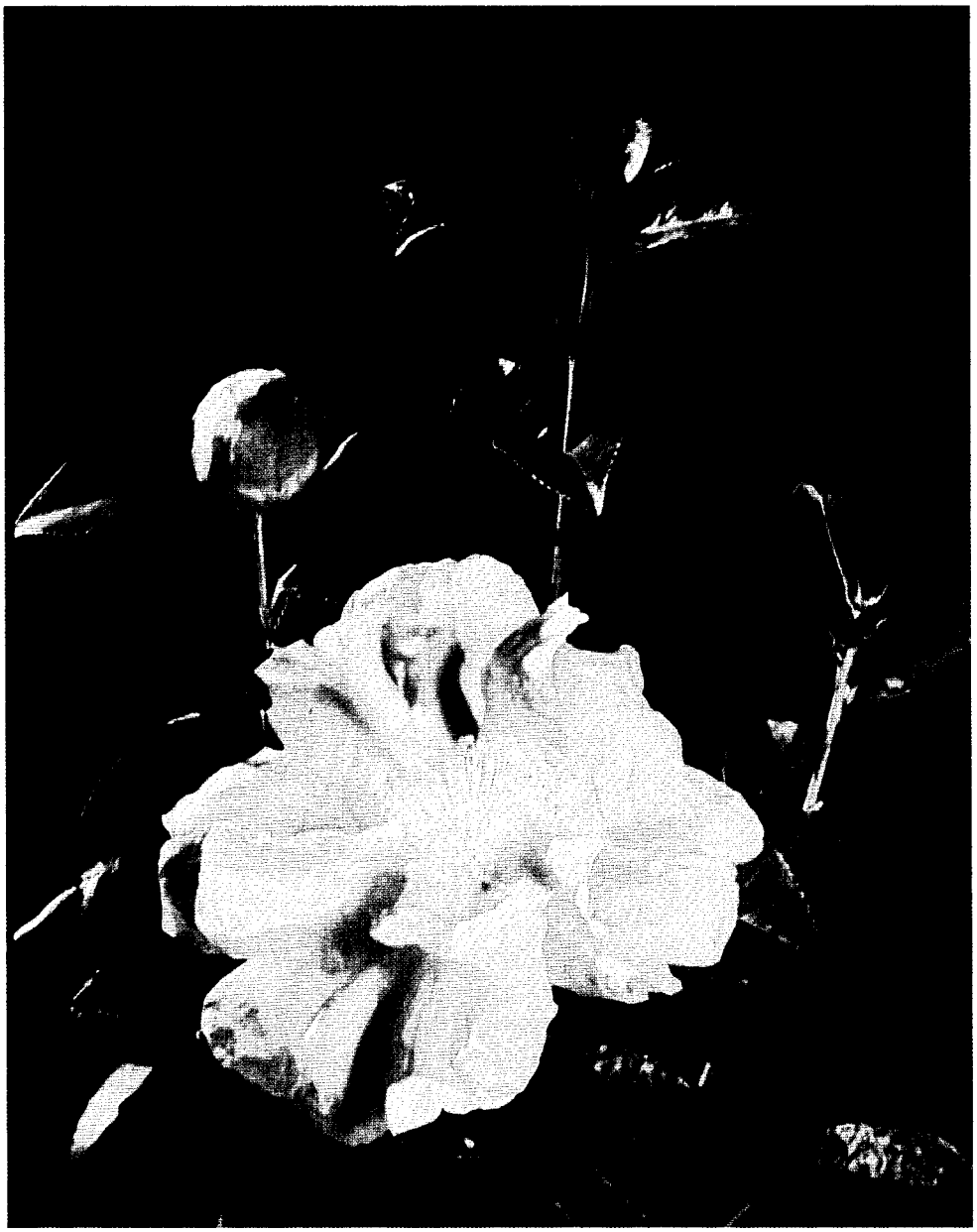
INVENTOR.
JAMES HOWARD ASPER
BY Rummler & Snow
Attys.

United States Patent Office

Plant Pat. 2,874
Patented Mar. 25, 1969

2,874

CAMELLIA PLANT

James Howard Asper, Escondido, Calif., assignor to Monrovia Nursery Company, Azusa, Calif., a corporation of California Filed Sept. 1, 1967, Ser. No. 665,189
Int. Cl. A01h 5/02
U.S. Cl. Plt.—61 1 Claim

ABSTRACT OF THE DISCLOSURE

A new camellia hybrid having a vigorous growth and early blooming habit and producing large spinel pink flowers continuously and profusely from early fall through early winter.

BACKGROUND OF THE INVENTION

My new variety of camellia plant originated as a seedling selected from a group produced by my crossing *C. sasanqua* Narumigata (unpatented) with *C. reticulata* Lion Head (unpatented) with the object of developing a camellia plant having the plant vigor and early blooming of *C. sasanqua* species and the large flower and beauty of the species *C. reticulata*. This new variety was discovered by me at my nursery grounds in Escondido, Calif. in 1960 and resulted from breeding efforts carried on by me and under my direction since 1957. Because the new plant showed many of the characteristics being sought, it was selected for further test and accordingly I have asexually reproduced the new plant by cuttings and grafting through several generations at Escondido, Calif. which work has demonstrated that all of the novel and unusual characteristics of the new plant are fixed and hold true from generation to generation.

DESCRIPTION OF THE DRAWING

My new variety of camellia plant is illustrated by the accompanying photographic drawing in which a fully opened bloom, a bud and foliage are shown in substantially natural color.

DESCRIPTION OF THE INVENTION

The following is a detailed description of my new variety of camellia plant, the color designation of bud and bloom being according to the Horticultural Colour Chart issued by the British Colour Council.

*The plant*

Origin: Seedling.
Parentage:
- *Seed parent.*—*C. sasanqua* Narumigata (unpatented).
- *Pollen parent.*—*C. reticulata* Lion Head (unpatented).

Classification: Hybrid.
Form: Bush, sturdy and upright.
Height: Eight feet.
Growth: Vigorous, strong and branching.
Foliage:
- *Quantity.*—Abundant.
- *Size of leaf.*—2½ inches long, 1½ inches wide.
- *Shape of leaf.*—Ovate with serrated margin.
- *Texture.*—Leathery and glossy.

- *Color.*—Upper side—dark green. Under side—light green.
- *Petioles.*—¼ inch long.
- *Ribs and Veins.*—Prominent.

*The bud*

Form: Globular.
Size: 1½ inches long, 1 inch in diameter. Opens slowly.
Color: Spinel Pink 0625—when sepals first divide and when petals begin to unfurl.
Sepals: Hooded over bud and branched. Color—pale green, inside and outside.
Calyx: Funnel shaped and broad, with hairy aspect. Calyx does not split.
Peduncle: 1/16 inch long; erect and hairy; and of pale green color.

*The flower*

Blooming habit: Profusely and continuous in season—early fall and early winter in its natural habitat.
Size: Large. 5½ inches in diameter, 2½ inches in depth.
Borne: Singly.
Shape: Cup-shaped when bloom first opens, tends to flatten as bloom matures.
Petalage:
- *Number of petals.*—14.
- *Arrangement.*—Loosely imbricate with downwardly curled margins.
- *Color.*—Spinel Pink 0625 at base, and throughout all petals on both sides.

Petaloids: None.
Peduncle: Sturdy, upright and of brownish green color.
Discoloration: Color fades slightly after full bloom.
Fragrance: Slight.
Lasting quality: Nine days on plant; three days as cut flower.
Persistence: Flower does not hang on and dry. The blooms are not affected by hot or wet weather and as observed at Escondido, Calif. the plant appears to be subject to no disease.

*Reproductive organs*

Stamens:
- *Anthers.*—Number 148—in bunched arrangement.
- *Filaments.*—Length—¾ inch. Color—pale yellow.

Pollen: Color—golden yellow.
Pistils: 3 in number. Color—light green.
Ovaries: Joined.

*Fruit*

The fruit is fertile, round in shape and of brown color at maturity.

I claim:

1. A new and distinct variety of camellia plant substantially as shown and described, characterized by its large blooms of Spinel Pink color and loosely imbricate petals of relatively large size, its vigorous plant growth habit and its profuse and continuous blooming during its early fall to early winter season.

No references cited.

ROBERT E. BAGWILL, *Primary Examiner.*